United States Patent [19]
Wood et al.

[11] Patent Number: 5,798,263
[45] Date of Patent: Aug. 25, 1998

[54] APPARATUS FOR QUANTIFYING DUAL-LUMINESCENT REPORTER ASSAYS

[75] Inventors: Keith V. Wood, Madison; Bruce A. Sherf, Waunakee, both of Wis.

[73] Assignee: Promega Corporation, Madison, Wis.

[21] Appl. No.: 708,533

[22] Filed: Sep. 5, 1996

Related U.S. Application Data

[60] Provisional application No. 60/003,284, Sep. 5, 1995.
[51] Int. Cl.$^6$ ...................................................... C12M 1/34
[52] U.S. Cl. ........................... 435/288.7; 435/287.2; 435/288.4; 422/52; 422/82.05; 250/361 C; 356/246
[58] Field of Search ........................ 435/6, 8, 288.3, 435/288.4, 288.7, 287.3, 287.2, 808; 422/52, 65, 82.05, 82.08; 436/172, 805; 250/361 C; 356/246

[56] References Cited

U.S. PATENT DOCUMENTS

| | | |
|---|---|---|
| 3,756,920 | 9/1973 | Kelbaugh et al. . |
| 4,235,961 | 11/1980 | Lundin . |
| 4,390,274 | 6/1983 | Berthold et al. . |
| 4,459,265 | 7/1984 | Berglund . |
| 4,755,055 | 7/1988 | Johnson et al. . |
| 4,772,453 | 9/1988 | Lisenbee ........................... 422/52 |
| 4,818,883 | 4/1989 | Anderson et al. . |
| 5,035,866 | 7/1991 | Wannlund . |
| 5,043,141 | 8/1991 | Wilson et al. . |
| 5,082,628 | 1/1992 | Andreotti et al. . |
| 5,139,745 | 8/1992 | Barr et al. . |
| 5,159,197 | 10/1992 | Wannlund . |
| 5,283,179 | 2/1994 | Wood . |
| 5,290,708 | 3/1994 | Ashihara et al. . |
| 5,316,726 | 5/1994 | Babson et al. . |
| 5,340,714 | 8/1994 | Katsilometes .................. 435/6 |
| 5,380,487 | 1/1995 | Choperena et al. . |
| 5,447,687 | 9/1995 | Lewis et al. .................... 422/52 |

FOREIGN PATENT DOCUMENTS 0025350  3/1981  European Pat. Off. .

OTHER PUBLICATIONS

Blaise, C., et al. (1994) BioTechniques: 16, 932–937.
Bronstein, I., et al., (1994) Anal–Biochem.: 219, 169–181.
Denburg, et al. (1969) Archives of Biochemistry and Biophysics: 134, 381–394.
Denburg, J.L., and McElroy, W.D. (1970) Archives of Biochemistry and Biophysics: 141, 668–675.
Flanagan, W. M. et al. (1991) J. Virology: 65, 769–786.
Jain, V. K. and Magrath, I. T. (1992) BioTechniques: 12, 681–683.
Kondepudi, T., et al., Poster abstract #725, presented at annual meeting of the American Society of Cell Biology, Dec. 10–14, 1994, San Francisco, CA.
Leckie, F. et al. (1994) BioTechniques: 17, 52–57.
Lee et al. (1970) Archives of Biochemistry and Biophysics: 141, 38–52.
Thompson, J. F., et al. (1991) Gene: 103, 171–177.

*Primary Examiner*—William H. Beisner
*Attorney, Agent, or Firm*—DeWitt Ross & Stevens SC

[57] ABSTRACT

The presently disclosed invention is drawn to an automatic luminometer apparatus capable of measuring two distinct luminescent reactions from within a single, non-compartmentalized sample container. The present apparatus may be dimensioned, configured, and programmed to automatically perform dual-reporter luminescent assays using multi-well sample plates, such as 96-well microtiter plates.

13 Claims, 9 Drawing Sheets

1. Optional - measure dark curent of photomultiplier

2. Optional - manually inject reagent into sample cuvette to initiate 1st luminescent reaction 3. Place sample cuvette into sample holder, seal enclosure 4. Optional depending on #2 - Automatically inject reagent into sample cuvette to initiate 1st luminescent reaction 5. Measure luminescence of 1st reaction 6. Transfer 1st luminescent signal to data storage means 7. Automatically inject "quench and activate" reagent(s) into sample cuvette to initiate 2nd luminescent reaction 8. Measure luminescence of 2nd reaction 9. Transfer 2nd luminescent signal to data storage means 10. Optional - inject quench reagent into sample cuvette 11. Optional - measure dark current of photomultiplier 12. Manipulate accumulated data via control means and output in desired format to output means

*FIG. 4*

1. Optional - measure dark current of photomultiplier

2. Align injector and photomultiplier with 1st well

3. Automatically inject reagent into well to initiate 1st luminescent reaction in well 4. Measure luminescence of 1st reaction 5. Transfer 1st luminescent signal to data storage means 6. Automatically inject "quench and activate" reagent(s) into well to initiate 2nd luminescent reaction in well 7. Measure luminescence of 2nd reaction 8. Transfer 2nd luminescent signal to data storage means 9. Optional - inject quench reagent into well 10. Optional - measure dark current of photomultiplier 11. Align injector and photomultiplier with next well 12. Repeat steps 3 through 11

13. Manipulate accumulated data via control means and output in desired format to output means

*FIG. 6*

APPARATUS FOR QUANTIFYING DUAL-LUMINESCENT REPORTER ASSAYS

This appllication claims the benefit of U.S. Privisional Application No. 60/003,284, filed Sep. 5, 1995.

FIELD OF THE INVENTION

The present invention is drawn to an apparatus for quantifying integrated, single-tube, dual-reporter luminescent assays. Specifically, the present invention relates to an apparatus which allows two distinct luminescent reactions to be assayed sequentially within a single, non-compartmentalized sample.

CITED REFERENCES

Full bibliographic citations to the references cited in this provisional application can be found in the Bibliography section.

DESCRIPTION OF THE PRIOR ART

Luminescence is produced in certain organisms as a result of luciferase-mediated oxidation reactions. Currently, luciferase genes from a wide variety of vastly different species, particularly the luciferase genes of *Photinus pyralis* (the common firefly of North America), *Pyrophorus plagiophathalamus* (the Jamaican click beetle), *Renilla reniformis* (the sea pansy), and several bacteria (e.g., *Xenorhabdus luminescens* and *Vibrio spp*), are extremely popular luminescence reporter genes. Reference is made to Bronstein, et al. (1994) for a review of luminescence reporter gene assays. Firefly luciferase is also a popular reporter for ATP concentrations, and in that role is widely used to detect biomass. Various other reporter applications of luciferases have been described in the scientific literature. Luminescence may be produced by other enzymes when mixed with certain synthetic substrates; such as alkaline phosphatase mixed with adamantyl dioxetanes, or horseradish peroxidase mixed with luminol.

Luciferase genes are widely used as genetic reporters due to the non-radioactive nature, sensitivity, and extreme linear range of luminescence assays. For instance, as few as $10^{-20}$ moles of the firefly luciferase can be detected. Consequently, luciferase assays of gene activity are used in virtually every experimental biological system, including both prokaryotic and eukaryotic cell cultures, transgenic plants and animals, and cell-free expression systems. Similarly, luciferase assays of ATP are highly sensitive, enabling detection to below $10^{-16}$ moles.

Luciferases generate light via the oxidation of enzyme-specific substrates, called luciferins. For firefly luciferase and all other beetle luciferases, this is done in the presence of magnesium ions, oxygen, and ATP. For anthozoan luciferases, including Renilla luciferase, only oxygen is required along with the luciferin. Generally, in luminescence assays of genetic activity, reaction substrates and other luminescence-activating reagents are introduced into a biological system suspected of expressing a reporter enzyme. Resultant luminescence, if any, is then measured using a luminometer or any suitable radiant energy-measuring device. The assay is very rapid and sensitive, and provides gene expression data quickly and easily, without the need for radioactive reagents. Reporter assays other than for genetic activity are performed analogously.

The conventional assay of genetic activity using firefly luciferase has been further improved by including coenzyme A (CoA) in the assay reagent to yield greater enzyme turnover and thus greater luminescence intensity. (Promega Luciferase Assay Reagent, Cat. No. E1500, Promega Corporation, Madison, Wis.; see U.S. Pat. No. 5,283,179, incorporated herein by reference.) Using this reagent, luciferase activity can be readily measured in luminometers or scintillation counters. The luciferase reaction, modified by the addition of CoA to produce persistent light emission, provides an extremely sensitive and rapid assay for quantifying luciferase expression in genetically altered cells or tissues.

The concept of a dual-enzyme reporter system relates to the simultaneous use and measurement of two individual reporter enzymes within a single system. In genetic reporting, examples that currently benefit from dual-reporter assays include individual cells or cell populations (such as cells dispersed in culture, segregated tissues, or whole animals) genetically manipulated to simultaneously express two different reporter genes. Most frequently, the activity of one gene reports the impact of the specific experimental conditions, while the activity of the second reporter gene provides an internal control by which all sets of experimental values can be normalized.

Cell-free reconstituted systems that may benefit from dual-enzyme reporter technology are cellular lysates derived for the simultaneous translation, or coupled transcription and translation, of independent genetic materials encoding experimental and control reporter enzymes. Immuno-assays may, likewise, be designed for dual-reporting of both experimental and control values from within a single sample.

Currently, genes encoding firefly luciferase (luc), chloramphenicol acetyl transferase (CAT), beta-galactosidase (lacZ), beta-glucuronidase (GUS) and various phosphatases such as secreted alkaline phosphatase (SEAP) and uteroferrin (Uf; an acid phosphatase) have been combined and used as co-reporters of genetic activity. The following references provide representative examples of these various reporter genes used in combined form for the purpose of dual-reporting of genetic activity: luc and GUS: Leckie et al. (1994); luc and CAT, and luc and lacZ: Jain and Magrath (1992); CAT and lacZ: Flanagan et al., (1991); SEAP and Uf: Kondepudi et al., (1994).

The performance of any dual-enzyme reporter assay is limited by the characteristics of the constituent enzyme chemistries and the ability to correlate their respective resulting data sets. Quantifying the combined expression of any two of the above reporters from within a single cell lysate necessitates splitting the sample so that the activity of each reporter can be assayed independently. Hence, the disparate enzyme kinetics, assay chemistries and incubation requirements, of these various reporter enzymes makes it impossible to combine them into an integrated, single-tube, dualreporter assay format. An ideal dual-reporter system would be comprised of two enzyme assays with compatible chemistries, and identical temperature and handling conditions, speed, sensitivity, and instrumentation required for detection.

For instance, U.S. Pat. Nos. 5,035,866 and 5,159,197, to Wannlund, describe a relatively simple apparatus for performing bioluminescent bacteriuria analysis. The analysis is based upon a measurement of bacterial ATP from any bacteria present in the urine sample. Before the luminescent reaction can be initiated, non-bacterial ATP must be removed from the sample so it will not result in a false positive reading. Wannlund utilizes multi-well test plates having corresponding upper and lower chambers. The urine sample is placed into the upper chamber and the chemicals necessary to remove non-bacterial ATP are added to the sample. After this reaction is completed, the sample is forced into the lower chamber by air pressure, where the reagents necessary to initiate the luminescent reaction are already in place. The sample plate is then mechanically biased against a conventional high-speed photographic film plate. Those samples testing positive for bacterial infection will emit a luminescent signal, thereby exposing the photographic film directly beneath that test well. The apparatus is qualitative, simple in operation, and does not require an external power source. This device, however, is solely qualitative in nature, and is incapable of rendering meaningful quantitative distinctions between luminescent samples.

U.S. Pat. No. 4,818,883 to Anderson et al. describes a luminometer apparatus in which a shutter is situated between the sample and a photo-detector. Light produced during a phosphorescent reaction is detected by the photo-detector and signals output from the photo-detector are applied to a circuit which samples the signals from the photo-detector at preset intervals. The successive values of the signals are subtracted from one another to determine a peak value of light intensity. Once the peak value of light intensity has been determined the shutter is interposed between the sample and the photo-detector and the dark current signal of the photo-detector is measured. The dark current signal is then subtracted from the peak measured value of the phosphorescent reaction. The true peak intensity of the emitted light from the phosphorescent reaction is thereby determined. To determine the concentration of the material being assayed in the sample, the peak intensity is raised to a given exponent, which value has been previously derived for the analyte being sampled. This arrangement of elements is similar to many common luminometers where the dark current of the photo-detector is determined, followed by acquisition of the sample signal, and subtraction of the dark current from the sample signal to determine the true luminescent intensity of the sample.

U.S. Pat. No. 5,290,708 to Ashihara et al. describes an apparatus for automatically performing immunoassays. The apparatus utilizes bifurcated cartridges having two separate components separated by a sealing film. The reactants for the immunoassay being performed are separately contained within the two compartments. The sealing film between the two compartments is broken to initiate the immuno reaction under study. The apparatus includes means to convey the cartridges along a reaction line where the immuno reaction is incubated and ultimately measured. The reaction line is steppingly movable and includes stations for diluting, stirring, washing, aspirating, and measuring the immuno reaction. The entire apparatus is controlled by a device having a memory storing operator which is capable of selecting programs for various measuring methods.

A similar automated immunoassay analyzer is described in U.S. Pat. No. 5,316,726 to Babson et al. This patent discloses a computer-controlled instrument capable of performing a wide variety of immunoassays and providing real-time presentation of the operations being performed by the instrument. The instrument is capable of performing more than one type of immunoassay on any one given sample. The movement of the immunoassay sample tubes through the apparatus is controlled by a bar code reader and a computer controller. The apparatus uses assay tubes which allow water to be expelled by centrifugal force, rather than by aspiration. This apparatus can measure immuno reactions using fluorescent, radioactive, or chemiluminescent labels.

Another automatic chemical analyzing device is described in U.S. Pat. No. 5,380,487 to Choperena et al. This computer-controlled device is an analyzer which permits automatic analysis of samples for multiple analytes using different assay protocols in a multiple chronology sequence, while operating on a predetermined and fixed length cycle. Here, certain standard steps, such as incubation, washing, and signal detection are assigned fixed operating sequences which begin and end within a fixed timing cycle. The fixed time duration allows samples to be transferred directly from one assay station to another without unnecessarily occupying any unused stations. In effect, each sample cuvette and each station within the apparatus are assigned a fixed time slot. This simplifies maximizing the throughput of the apparatus while minimizing the complexity of the logic and control of the various assay stations.

European Patent Application 0 025 350 to Holley describes an apparatus for detecting luminescent reactions in multi-well plates. The apparatus includes a plurality of liquid injector tubes situated above the multi-well plate and a corresponding plurality of photo-detectors situated below the multi-well plate. An entire row of sample wells are positioned in registration with both the liquid injector tubes and the photo-detectors. Reagents are then injected into the sample wells to initiate a luminescent reaction within each sample well. The luminescence generated by these reactions is then measured by the photo-detectors. The entire process is then repeated by positioning the next row of sample wells in registration with the injector tubes and photo-detectors. This reference does not comprehend an apparatus in which more than one reagent, or more than one distinct luminescent reaction is assayed within each sample.

Related devices for automatically analyzing luminescent reactions within a plurality of separate sample cuvettes are described in U.S. Pat. No. 3,756,920 to Kelbaugh et al., U.S. Pat. No. 4,459,265 to Berglund, and U.S. Pat. No. 4,755,055 to Johnson et al. These references all describe various arrangements for transporting a plurality of sample cuvettes into operational relationship with an injector and photomultiplier tube for initiating and quantifying a luminescent reaction within the sample. Like the above references, none of these references described performing a dual-luminescent assay within a single sample.

U.S. Pat. No. 5,043,141 to Wilson et al., U.S. Pat. No. 5,082,628 to Andreotti et al., and U.S. Pat. No. 5,139,745 to Barr et al. all describe luminometer devices having an injector apparatus situated above a sample to be tested, and a photo-detector situated below the sample. The injector adds the necessary reagents to initiate a luminescent reaction, whose energy is then detected by the photo-detector.

A major drawback to the use of luminescence assays in high-throughput applications is their incompatibility with standard laboratory equipment. For instance, it is not possible to quantify luminescence reactions contained in clear multi-well plates with precision or accuracy because of the internal refraction of light through the optically clear plate. FIG. 1 demonstrates that, when using conventional 96-well clear polystyrene microtiter plates, the luminescence signal generated in one well is refracted through the plastic over relatively long distances. Hence, the light refracted from one luminous sample can interfere with the subsequent measurement of signal from luminescent samples in successive wells. FIG. 2 shows the cumulative nature of refracted light emanating from multiple luminous samples within a single clear plastic plate. While the luminescent signal in the first sample well can be measured accurately, sequential activation of luminescent reactions in following wells leads to increasingly inaccurate measurements due to the cumulative emission of photons refracted through the plastic from all previous samples. This problem of refracted light, or "refractive cross-talk" is further exacerbated when brightly illuminated wells are situated adjacent to negative control wells in which no luminescence is generated, or when brightly lit wells are situated near relatively dim wells. This makes determining the absolute and baseline luminescence in a clear multi-well plate difficult, if not impossible.

Multi-well plates made from opaque plastics such as white and black polyethylene are commercially available (e.g., DynaTech Laboratories, Chantilly, Va.; Labsystems, Helsinki, Finland; NUNC, Roskilde, Denmark), and are now being adopted to prevent refractive cross-talk between samples in applications involving high-throughput luminometric analysis (Blaise, C., et al., 1994). However, while the reflectivity of white plastic yields greater luminescence sensitivity than clear plates, photons are readily scattered from the walls of adjacent wells, again introducing cross-talk interference between wells. Here, the cross-talk is referred to as "reflective cross-talk." In the same manner as refractive cross-talk, reflective cross-talk is particularly evident when assaying dim wells (such as negative controls not containing luciferase) that are adjacent to bright wells. Black 96-well plates, originally intended for fluorescent applications, are not ideal for luminescence applications because the sample signal is greatly diminished due to the non-reflective nature of the plastic.

Regardless of color, the cost of opaque plates as compared to conventional transparent plates is substantial. Opaque plates currently cost approximately $5 to $6 each, as compared to transparent plates which normally retail for less than half that amount. For example, sterile opaque 96-well plates and lids are offered by DynaTech Laboratories at a combined retail cost of $286 per set of 50, or $5.72 per each. Similarly treated transparent 96-well plates with lids are manufactured by Corning (Corning, N.Y.) and can be purchased at a retail cost of $110 per 50, or $2.20 per each.

In addition to their cost, opaque plates impose technical limitations not associated with clear multi-well plates. For example, many researchers desire to expedite their assay operations and reduce the cost of materials by culturing cells directly in the wells of the microplate used to perform the final assay. Opaque plates are inferior for this purpose because:

i) cultured cells cannot be viewed or photographed through the opaque plate;

ii) the composition and surface characteristics of opaque plastics are different from those of standard cell culture-grade plastic-ware, and have undetermined effects on cell adhesion and growth characteristics; and iii) sterile, cell-culture grade opaque plates and covers (packaged separately) are not widely available.

One manufacture (Packard, Meridian, CT) recognized the technological problems associated with opaque plates and responded by developing a specialty plate consisting of an opaque plastic body with a clear plastic bottom (sold under the name "View Plate", product #600-5181). However, the availability of such specialty plates is limited, and the high price ($6 each) of such a consumable product is generally prohibitive for highthroughput users in both academic and private laboratories.

The 1991 publication of Thompson et al. presents findings on the use of substrate analogs (benzothiazole, phenylbenzothiazole, and hydroxy-phenylbenzothiazole) to induce conformational changes in firefly luciferase. Thompson et al. demonstrate that, when bound to the luciferase enzyme, said chemical compounds provide increased in vivo and in vitro stability to the luciferase enzyme by conferring greater resistance to proteolytic degradation. Though analogs to beetle luciferin are inhibitors of firefly luciferase activity, the assay of luciferase activity from treated samples was performed using diluted cellular extracts containing sub-inhibitory concentrations of the various residual substrate analogs.

U.S. Pat. No. 4,235,961 to A.T. Lundin describes a method for the photometric determination of subunit B of creatinine kinase. The assay proceeds in the presence of the L-luciferin enantiomer of the natural beetle luciferase substrate (D-luciferin), which acts as a competitive inhibitor of the luciferase/D-luciferin reaction. Inhibition of the photometric reaction provides a more continuous emission of light from the sample, thereby allowing the kinetics of creatine kinase reaction to be studied.

U.S. Pat. No. 4,390,274 to Berthold et al. describes a photometric assay in which an additional luminescence substrate is added to a sample after a first experimental photometric measurement is taken. A second photometric measurement is then taken. The added substrate is chemically distinct from the experimental substrate being measured, but is a reaction partner in the same luminescence reaction system that is photometrically determined in the first measurement. The added substrate is used for internal standardization of each sample.

Various other publications describe chemical compounds which will reduce the luminescence of a luciferase reaction, but in none of these is this reduction of purposeful value in itself. Denburg and McElroy (1970) present findings on the interaction of selected anions as inhibitors of the firefly luciferase luminescent reaction. Thiocyanate, iodide, nitrate, bromide and chloride are found to have varying inhibitory interaction with the luciferase enzyme. Lee et al. (1970) and Denburg et al. (1969) present findings on various competitive inhibitors of the firefly luciferase luminescent reaction.

None of the above references, taken alone, or in any combination, are seen as describing the presently disclosed invention.

SUMMARY OF THE INVENTION

A first embodiment of the present invention is an apparatus for quantifying integrated photon-generating assays. These assays utilize two distinct photon-generating reactions within a non-compartmentalized sample container. The apparatus comprises sample holding means which are dimensioned and configured to releasibly grip a non-compartmentalized sample container workpiece and injecting means for sequentially injecting distinct first and then second reagents into the sample container workpiece at a user-defined time interval. The apparatus further includes photon measuring means for measuring photons emanating from the sample container workpiece and generating signals proportional to the measured photons. Specifically, the photon measuring means are dimensioned and configured to sequentially generate a first corresponding signal subsequent to injection of the first reagent into the sample container workpiece and a second corresponding signal subsequent to injection of the second reagent into the sample container workpiece. Signal storage and retrieval means are provided for storing and retrieving the first and second signals; the signal storage and retrieval means being operationally linked to the photon measuring means. The invention further includes programmable control means operationally linked to and dimensioned and configured to control overall operation of the injecting means, the photon measuring means, and the signal storage and retrieval means. The programmable control means are further dimensioned and configured to perform mathematical manipulations on the first and second signals generated by the photon measuring means. The apparatus also includes display means to display the first and second signals and any mathematical manipulations performed thereon.

A second embodiment of the invention is drawn to a high-throughput apparatus for quantifying integrated photon-generating assays. Here, the invention is specifically designed to perform high-throughput assays which utilize two distinct photon-generating reactions within a non-compartmentalized sample container. Here the apparatus comprises movable sample holding means dimensioned and configured to releasibly grip a 96-well microtiter sample container workpiece in which each individual well of the microtiter plate is non-compartmentalized and one or more cooperating pairs of first and second injecting means for sequentially injecting distinct first and then second reagents, respectively, into an individual well of the sample container workpiece at a user-defined time interval. The apparatus further includes one or more corresponding photon measuring means for measuring photons emanating from the individual wells of the sample container workpiece and generating signals proportional to the measured photons. The photon measuring means are dimensioned and configured to sequentially generate a first corresponding signal subsequent to injection of the first reagent into the sample container workpiece and a second corresponding signal subsequent to injection of the second reagent into the sample container workpiece. Signal storage and retrieval means are provided for storing and retrieving the first and second signals; the signal storage and retrieval means being operationally linked to the photon measuring means. Programmable control means are operationally linked to and dimensioned and configured to control movement and operation of the sample holding means, the injecting means, the photon measuring means, and the signal storage and retrieval means. The programmable control means are further dimensioned and configured to perform mathematical manipulations on the first and second signals generated by the photon measuring means. Display means are provided to display the first and second signals and any mathematical manipulations performed thereon. This embodiment of the present invention is specifically designed to perform one or more dual reporter, photon-generating reactions within a 96-well microtiter workpiece.

As in the preceding embodiments, a third embodiment of the present invention is directed to an apparatus for quantifying integrated photon-generating assays which utilize two distinct photon-generating reactions within a non-compartmentalized sample container. The apparatus comprises sample holding means which are dimensioned and configured to releasibly grip a non-compartmentalized sample container workpiece, as well as first injecting means for injecting a first reagent into the sample container workpiece. Photon measuring means are provided to measure photons emanating from the sample container workpiece at a user-defined time interval subsequent to injection of the first reagent and for generating a signal proportional to the measured photons. The apparatus further includes second injecting means for injecting a second reagent into the sample container workpiece at a user-defined time interval subsequent to injection of the first reagent. Photon measuring means for measuring photons emanating from the sample container workpiece at a user-defined time interval subsequent to injection of the second reagent and for generating a signal proportional to the measured photons are also provided. Here, it is preferred that the photon measuring means for measuring photons emanating from the sample container workpiece at a user-defined time interval subsequent to injection of the first reagent and the photon measuring means for measuring photons emanating from the sample container workpiece at a user-defineed time interval subsequent to injection of the second reagent are one in the same. Signal storage and retrieval means are included for storing and retrieving the first and second signals; the signal storage and retrieval means being operationally linked to the photon measuring means. This embodiment of the invention also includes programmable control means which are operationally linked to and dimensioned and configured to control operation of the first and second injecting means, the photon measuring means, and the signal storage and retrieval means. The programmable control means are further dimensioned and configured to perform mathematical manipulations on the first and second signals generated by the photon measuring means. Display means are provided to display the first and second signals and any mathematical manipulations performed thereon.

In all of the embodiments described above, it is preferred that the injecting means includes an outflow orifice disposed adjacent to the sample container workpiece, and that the outflow orifice, the sample holding means, and the photon measuring means are disposed within a light-tight enclosure.

A principal aim and object of the present invention is to provide an automatic luminometer apparatus dimensioned and configured to allow the sequential quantification of two separate and distinct luminescent reactions within a single, non-compartmentalized sample container.

Another aim of the present invention is to provide an automatic luminometer apparatus dimensioned and configured to allow automatic and high-throughput analysis of dual-reporter luminescent assays contained within conventional 96-well microtiter plates.

Yet another aim of the present invention is to provide an automatic luminometer apparatus dimensioned and configured to automatically perform dual-luminescent reporter assays which employ two distinct luciferase luminescent systems within each sample.

Still another aim of the present invention is to provide an automatic luminometer apparatus which is dimensioned and configured to accommodate a wide variety of sample containers, including single-sample containers and multi-well sample containers.

A further aim of the present invention is to provide an automatic luminometer apparatus dimensioned and configured to allow post-acquisition manipulation of data to yield meaningful information about the samples assayed.

A still further aim of the present invention is to provide an automatic and programmable luminometer apparatus dimensioned and configured to allow the sequential quantification of two separate and distinct luminescent reactions within a single, non-compartmentalized sample container.

Yet another aim of the present invention is to provide an automatic and programmable luminometer apparatus dimensioned and configured to allow automatic and high-throughput analysis of dual-reporter luminescent assays contained within conventional 96-well microtiter plates.

In many reporter applications, particularly genetic reporter applications, two distinct reporters are needed to yield valid or precise analytical data. In the prior art of enzymatic reporters, these reporters are assayed by separate and independent measurements of enzymatic activity. The results of these separate assays are then combined into a common analysis. This analytical method requiring two enzymatic reporters can be improved by combining both measurements of enzymatic activities into a single integrated assay process, and further improved by performing the method on a device capable of carrying out the integrated assay process and the subsequent data analysis. Such an analytical method is possible using two enzymatic reporters capable of generating luminescence in their respective assay of enzymatic activity.

The present invention provides an apparatus to perform such dual-luminescence assays. The invention relates to luminescence assays which include at least one reagent which rapidly quenches a given luminescence reaction, and simultaneously initiates a second luminescence reaction within the same sample container. Preferably, the second luminescence reaction is initiated without any extended incubation or delay between the two luminescent reactions. The present apparatus is capable of measuring the first luminescent signal, injecting quench reagents and activate reagents into the sample, and separately measuring the second luminescent signal. The present invention allows such dual-luminescence assays to be performed with minimal operator input, using any type of sample container, including 96-well microtiter plates.

The present invention relates to an automated luminometer apparatus which is capable of acquiring, storing, and manipulating signals generated from two distinct luminescent reactions from within a single sample contained in a single, non-compartmentalized vessel. By non-compartmentalized it is meant that the vessel in which the reaction is initiated and measured defines a single, undivided, and contiguous volume of space, such as a test tube, or a single well of a multi-well plate. The luminescent measurements are taken sequentially, with the first luminescent signal being measured and quenched prior to, or simultaneous with, the initiation of the second luminescent signal. The device is automated and includes movable means for measuring and quantitating luminescent energy, movable means for injecting reagents into single or multi-well sample containers, means to manipulate the sample container(s), optional programmable input means for programming the apparatus, data storage, output, and display means for compiling the information gathered by the luminescent measuring means and presenting the information in a meaningful and/or convenient fashion, and master control means for coordinating the various functions of the means described above.

The preferred type of assay to be performed by the apparatus is an integrated dual-enzyme luminescent assay which utilizes one or more reagents to rapidly and efficiently quench enzyme-mediated luminescent reactions. Two distinct luminescence reactions are sequentially initiated and measured within each sample tested. The distinct nature of the two luminescent reactions allows them to be initiated and quantified within a single, non-compartmentalized reaction vessel, without interference between the two reactions. This allows two separate and distinct measurements to be taken from a single sample without the need to subdivide the sample into two or more portions for testing.

For sake of brevity and clarity, the present specification shall concentrate solely on enzyme-mediated luminescent reactions, and particularly luciferase-mediated reactions. However, the presently disclosed invention functions equally well in assays utilizing other, non-enzymatic, photon-generating reactions, including phosphorescent, fluorescent, and chemiluminescent assays. The following discussion is not limiting in any fashion, and all functional or structural descriptions of the disclosed apparatus applied solely to enzyme-mediated, or luciferase-mediated, assays applies with equal force to the other non-enzyme-mediated luminescent assays described immediately above.

An enzyme-mediated luminescence reaction is any chemical reaction which yields photons as a consequence of the reaction, and uses an enzyme to effectively enable the reaction. Examples include luciferases isolated from a variety of luminous organisms, such as the firefly luciferase of *Photinus pyralis* or the Renilla luciferase of *Renilla reniformis*.

Luciferases are organized into groups based on the commonality of their luminescent reactions. Generally, the luciferases within a given group are derived from related luminous organisms, and catalyze the same chemical reaction. For instance, beetle luciferases, all catalyze ATP-mediated oxidation of beetle luciferin. In contrast, anthozoan luciferases catalyze oxidation of coelenterazine. Other enzymes in addition to luciferases mediate luminescent reactions using both natural and synthetic substrates. A commonly used example of this type of luminescent reaction is the reaction of luminol with horseradish peroxidase. Another example would be alkaline phosphatase which catalyzes a reaction with adamantyl 1,2-dioxetane phosphate.

The present apparatus is specifically designed to enable the quantification of two distinct luciferase-mediated reactions which are initiated sequentially within a single sample container. In short, the present apparatus includes means for initiating a first luminescent reaction, means for quantifying the luminescent energy generated by the first luminescent reaction, means for quenching the first luminescent reaction, means for initiating a second and distinct luminescent reaction, means for quantifying the luminescent energy produced in the second luminescent reaction, and means for outputting the data so gathered in various formats which provide useful information to the user.

It is preferred that the above means be dimensioned and configured to accommodate multiple sequential assays within conventional 96-well microtiter plates. Such microtiter plates can be either clear or opaque.

A unique advantage of the present apparatus is that it allows two distinct luminescent reactions to be quantified within a single sample without the need to either divide the sample into two portions for testing, or the need to use sub-divided sample containers. This is extremely beneficial for testing done on small samples. It is also cost-effective because standard sample containers are used, rather than specialized equipment designed specifically for the disclosed luminometer.

The present apparatus is also automatic and optionally programmable to achieve high-throughput testing of samples contained in multi-well microtiter plates with minimum user input.

BRIEF DESCRIPTION OF THE DRAWINGS

FIG. 4 is a flow chart showing operation of a first embodiment of the presently described invention.

FIG. 6 is a flow chart showing operation of a second embodiment of the presently described invention.

DETAILED DESCRIPTION OF THE INVENTION

Of particular interest in the present invention is a luminometer apparatus which utilizes novel "quench-and-activate" reagents for performing dual-reporter luminescent assays. Quench-and-activate reagents are novel assay reagents which selectively extinguish one luminescent reporter enzyme while simultaneously initiating another distinct enzyme-mediated luminescence reaction. The preferred protocol is to initiate and measure the second luminescent reaction promptly after the first luminescent reaction is extinguished, without any extended delay or incubation period. Preferably, the second luminescent reaction is initiated within one minute after the first luminescent reaction is extinguished. This assay allows for the sequential measurement of two separate and distinct luminescent reporters within one sample. The presently described apparatus is a device for automatically performing a dual-reporter luminescent assay.

A great benefit of the dual-reporter assay is that one of the luminescent reporters can be used as an internal standard, while the other luminescent reporter is used to report the impact of the experimental variables. In operation, one of the two enzyme-mediated luminescence reactions is first initiated by addition of a first initiating reagent or reagents into the experimental system. The luminescence signal produced by the first enzymatic reaction is then measured. The first enzymatic reaction is then specifically and selectively quenched by adding a quench-and-activate reagent which simultaneously quenches the first enzymatic reaction and initiates a second enzymatic reaction. The quench and activate reagent may be a single mixture of components (as in a solution), or may be two separate mixtures added to the reaction by separate means. The luminescent signal produced by the second enzymatic reaction is then measured in the same fashion as the first reaction. The information is stored in retrievable storage means, preferably magnetic storage media, and output to an output device, such as a CRT screen.

As a research tool for molecular biologists, luminescent enzyme reporter systems are more sensitive than the other, more traditional, enzyme reporter systems. Luciferase assays, in particular, are also much more rapid than those of other enzyme reporter systems. These features make luminescence-generating enzymes the preferred reporters of genetic and physiological activity.

Figure 1:
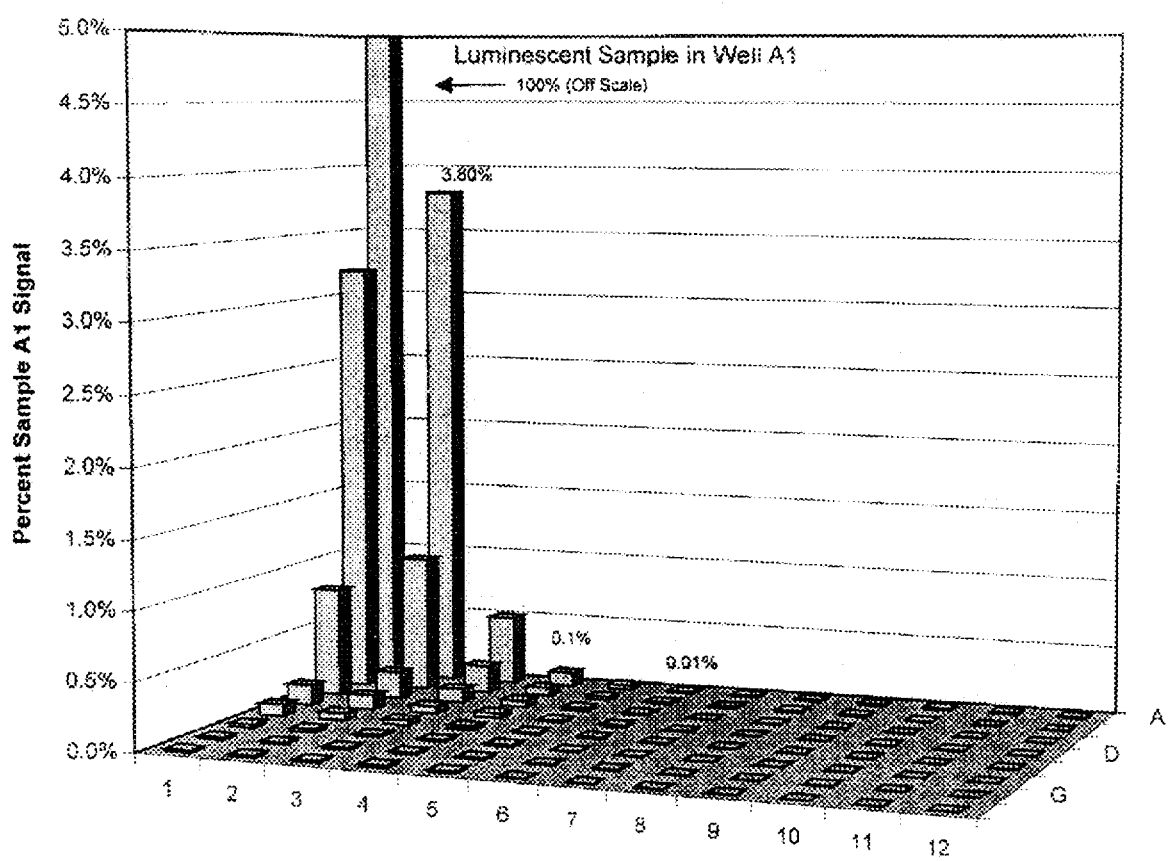
FIG. 1 is a three-dimensional graph showing prior art signal cross-talk radiating from a single luminescent sample within a clear plastic, 96-well microplate.
Figure 2:
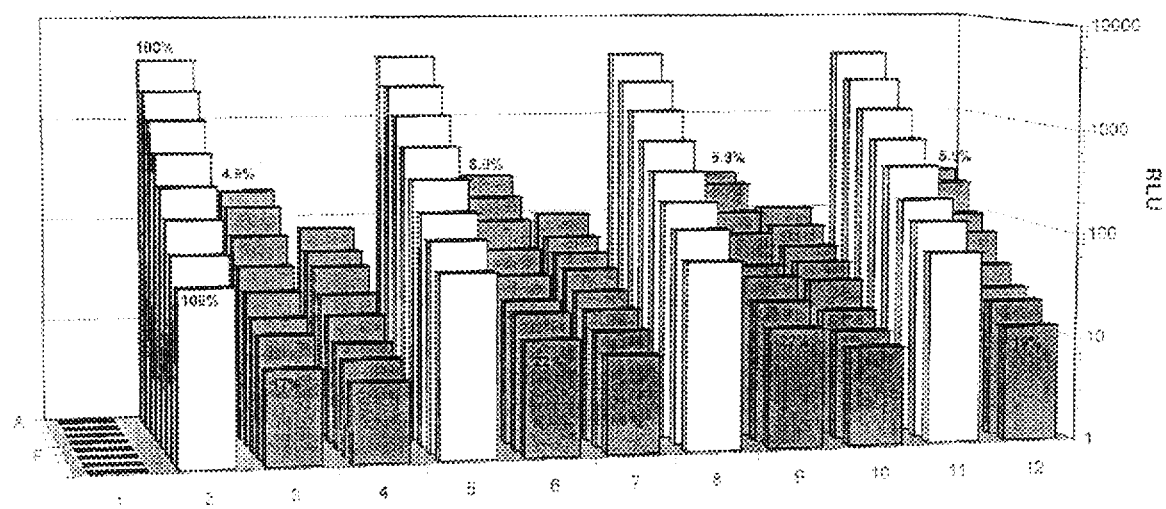
FIG. 2 is a three-dimensional graph showing the prior art cumulative nature of signal cross-talk radiating from multiple luminescent samples within a clear plastic, 96-well microplate.
Figure 3:
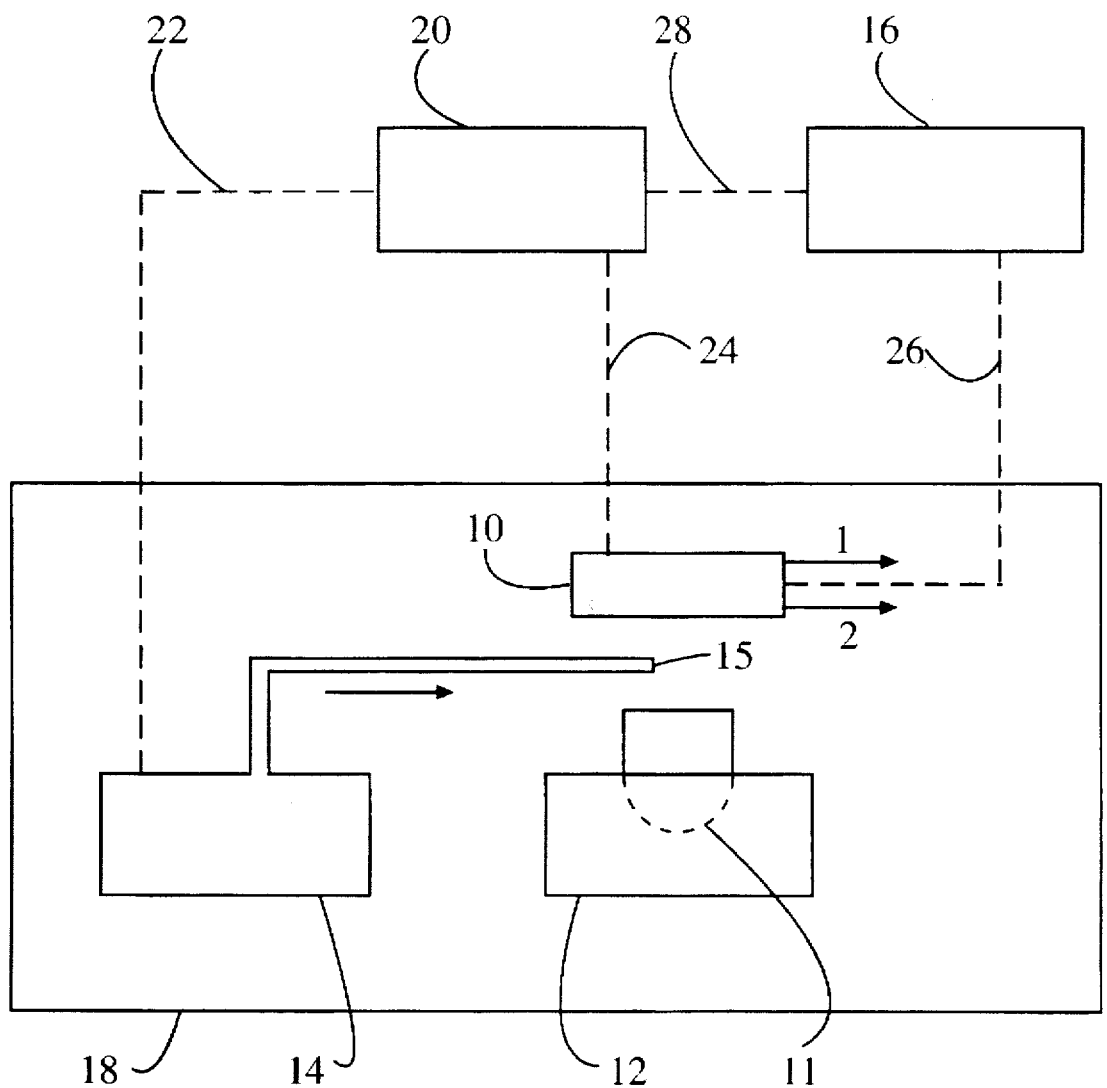
FIG. 3 is a schematic diagram of a first embodiment according to the present invention.

A first embodiment of the present invention is shown in schematic form in FIG. 3. Reference 10 designates a photon-detector which may be static or movable. If movable, the photon-detector can be translated in both the vertical and horizontal axes to allow easy access and maintenance of the entire apparatus. This movement is accomplished by conventional mechanical, electromechanical, or magnetic means, such as servomotors, solenoids, etc. The photon-detector can be of any conventional design, including a single or compound photomultiplier tube, a charge-coupled device (CCD), or similar device capable of accurately measuring luminescent energy.

The photon-detector senses the energy of a luminescent reaction and produces output signals corresponding to the intensity of the luminescence measured. A sample cuvette 11 is placed within a sample holder 12, the sample holder 12 being situated in operational relationship to the photon-detector 10. The sample holder 12 may also be movable or static. If movable, the sample holder is preferably translatable in either or both the vertical and horizontal axes to allow flexible positioning of samples, and convenient access for loading and unloading samples. The sample cuvette 11 may be a single sample container, as shown in FIG. 3, or a multi-well container, such as a 96-well microtiter plate.

One or more reagent injectors 14 is situated in operational relationship to the sample holder 12 and the sample cuvette 11. An injector output orifice, 15 is disposed adjacent to the sample container workpiece. The reagent injector 14 is capable of injecting liquid or solid reagents via the injector output orifice 15 into the sample cuvette 11 when the cuvette is placed within the sample holder 12. The reagent injector can be an assembly whereby one or more liquids are forced from one or more reservoirs through a conduit by a peristaltic pump, a vacuum-controlled aspirator, a reciprocating pump, and the like. For solid reagents, the reagent injector may be a conveyor belt, screw conveyor, etc.

In terms of overall functionality, the reagent injector 14 and injector output orifice 15 may be any type of conventional assembly dimensioned and configured to deliver material to a given location without limitation.

The reagent injector outflow orifice 15, sample holder, sample cuvette, and photon-detector are enclosed within a light-tight enclosure 18. The enclosure may comprise a suitably opaque lid or cover which encloses the various sub-assemblies, and includes a movable closure to allow access to the interior thereof.

The entire apparatus is controlled by a controller 20 operationally linked to the various components of the apparatus by a plurality of control lines 22, 24, 26, and 28. As depicted schematically in FIG. 3, a data storage and retrieval device 16 is operatively linked to the photon-detector 10 to store data quantified by the photon-detector. The data storage and retrieval device 16 is also controlled by the controller 20.

The controller 20 can be any type of controller known in the art. This includes, but is not limited to, programmable computer control means, microprocessors, digital signal processors, LSI chips, VLSI chips, ELSI chips, RISC processors, analog to digital converters and signal processors, digital to analog converters and signal processors, read only memory chips (ROM), erasable programmable read only memory chips (EPROM), conventional electric circuitry, conventional electronic circuitry, or mechanical means.

The control means 20 may be programmable. By "programmable," it is meant that the control means 20 may be dimensioned and configured to store and execute one or more pre-determined instruction sets entered either by the end-user (end-user programmability), or pre-determined and fixed at the time of manufacture (factory-fixed programmability). Flexible, end-user programmability allows the user to adapt the apparatus to perform various dual-reporter assay protocols to fit a given need. Factory-fixed programmability provides lower cost and ease of operation for fixed protocols.

The data storage and retrieval device 16 may be any such device known to the industry, including, but not limited to, magnetic storage media without limitation, including floppy disk drives, hard disk drives, and tape drives; magneto-optical storage media without limitation including WORM drives and erasable magneto-optical media; optical storage media without limitation, such as compact discs, LASER discs, and the like, random access memory chips (RAM), or conventional electric and/or electronic storage circuitry, or conventional mechanical storage means, such as punch cards.

The control lines 22, 24, 26, and 28 can be conventional wire connectors, such as coaxial cables, 10-pin connectors, SCSI connectors, and the like, which are capable of transmitting signals to and from the control means 20 to the various components of the present apparatus. The control lines can also be optical fiber cable, or wireless electromagnetic frequency control lines, such as infrared or microwave transmitters capable of receiving and transmitting signals to and from the control means, 20.

The invention may also include display means, such as a cathode ray tube or printer device, means for entering programming and other information into the controller, such as a keyboard, as well as an output means for outputting data compiled by the data storage and retrieval device.

A flow chart depicting the general operation of the first embodiment of the present invention is shown in FIG. 4. The operator of the device shown in FIG. 3 begins the assay by optionally measuring the dark current of the photon-detector 10. The operator may then optionally initiate the first luminescent reaction manually (step 2). This is done within the sample cuvette 11. The sample cuvette is then placed within the sample holder 12, and the light-tight enclosure 18 sealed to prevent ambient light from interfering with measurement of the luminescent energy generated by the reaction (step 3). Otherwise, the sample cuvette is placed into the luminometer, and the first initiating reagent is injected into the sample automatically (step 4).

The luminescence energy of the first enzyme-mediated luminescent reaction is then measured by the photon-detector 10, and the measured signal sent to the data storage and retrieval device as shown by arrow number 1 of FIG. 3. (Steps 5 and 6 of FIG. 4). One or more "quench-and-activate" reagents are then injected into sampled cuvette 11 via the reagent injector 14 through the output orifice 15 (step 7). As noted above, the quench-and-activate reagent(s) quenches the first luminescent reaction prior to, or while simultaneously initiating a second luminescent reaction. The photon-detector 10 is then used to measure the luminescent intensity of the second enzyme-mediated luminescent reaction. This second signal, designated by arrow number 2, is then output to the data storage and retrieval device 16. (Steps 8 and 9.) Optional steps here include injecting a quench reagent into the sample, and again measuring the dark current of the photon-detector. The first and second signals may then be manipulated using the control means 20 to yield meaningful results, such as a ratio of the two signals.

As noted above, the actual quantitation of the luminescent reactions takes place within the light tight enclosure 18.

Figure 5:
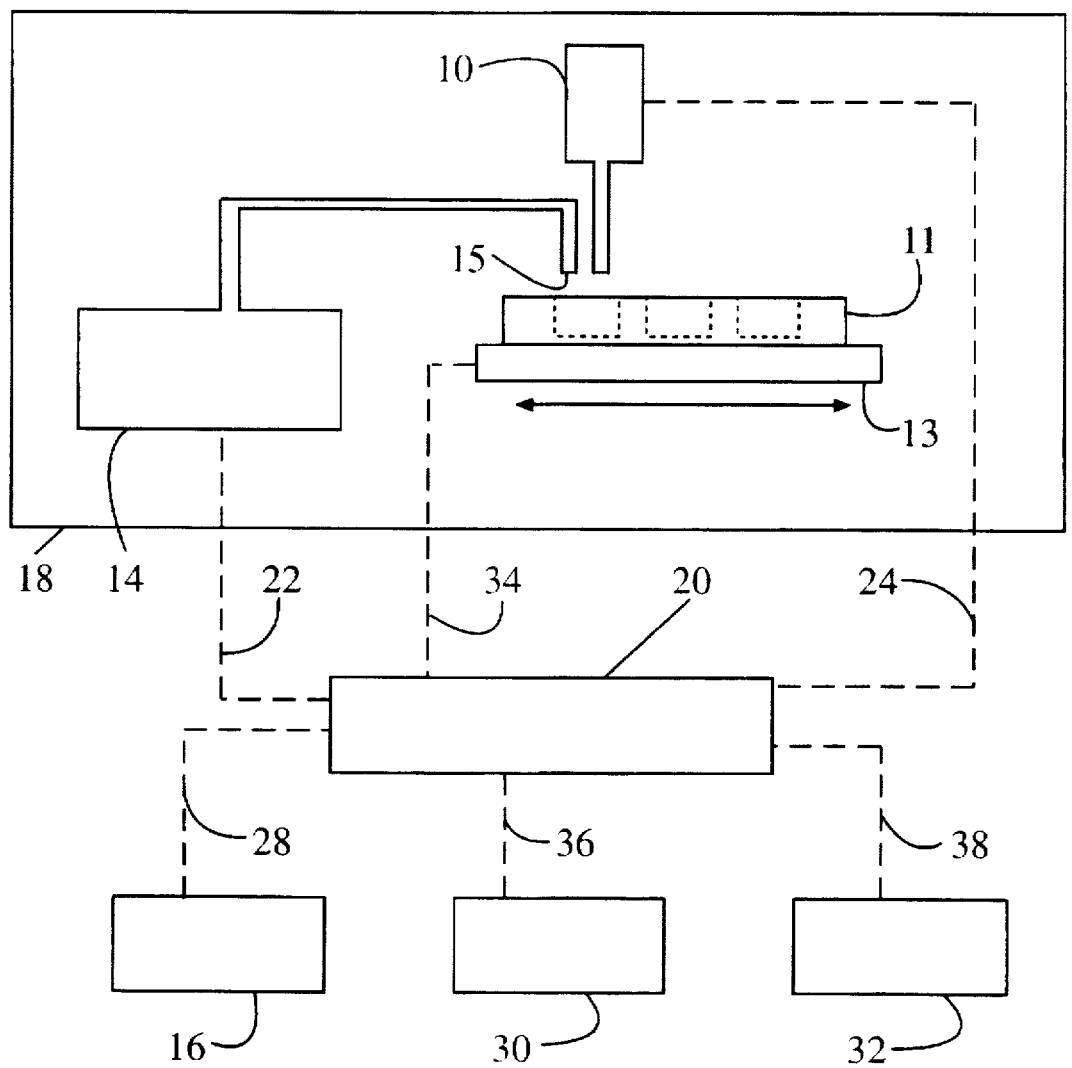
FIG. 5 is a schematic diagram of a second embodiment of the present invention including a computer controller, a keyboard to input programming data, and output and storage means.

A second and preferred embodiment of the present invention is shown in FIG. 5. Here, the photon-detector 10, reagent injector 14, injector output orifice 15, light-tight enclosure 18, controller 20, and data storage and retrieval means 16, are the same as described for FIG. 3. Additionally, it must be noted that there may be a plurality of photon-detectors 10 and reagent injectors 14 in order to maximize sample throughput. Such duplication of functional parts can be accomplished by mounting a plurality of the reagent injectors and photon-detectors upon a movable boom which enables the injectors and photon-detectors to be accurately positioned in operational relationship to multiple samples simultaneously. In this fashion, a plurality of samples can be analyzed simultaneously.

In the embodiment represented in FIG. 5, the sample holder 11 is a multi-well sample holder, such as a conventional 96-well microtiter plate. The plate 11 rests upon a movable stage 13 which is dimensioned and configured to position the plate into operational relationship with the photon-detector 10 and the reagent injector output orifice 15. The movable stage may also include releasible anchoring means for securely and releasibly fastening the multi-well plate to the stage. Preferably, the movable stage 13 is translatable in the horizontal plane, as indicated by the double arrow. Additionally, the movable stage may be translatable in the vertical axis to facilitate the initial loading and ultimate removal of the plate 11 from the apparatus. (This also allows the apparatus to accommodate non-standard sample holders of different sizes.)

Also, both the photon-detector 10 and the reagent injector output orifice 15 may be translatable to facilitate ease of operation, access, and maintenance of the disclosed apparatus. Movement of the stage, photon-detector, and reagent injector may be controlled by, for instance, a worm-screw rotated by a stepping motor. Servo-motors, hydraulic controls, pneumatic controls, and other conventional means for controlled movement may also be employed with equal success.

The preferred apparatus depicted in FIG. 5 also includes a data entry device 32 and a data display device 30. The data entry device 32 is preferably a standard keyboard entry device.

The display device 30 may be a standard cathode-ray tube screen or light-emitting or liquid crystal diode display, and/or a hard-copy display device, such as a means for printing accumulated data. Such devices are well known and widely used.

The control lines 22, 24, 28, 34, 36, and 38 are the same as those described for FIG. 3.

The operation of the luminometer device described in FIG. 5 is shown in flow-chart form in FIG. 6. Preliminarily, the multi-well plate 11 is placed into the apparatus, releasibly anchored to the movable stage 13, and the light-tight enclosure 18 is then sealed. The subsequent actions taken by the apparatus are initiated by commands entered from the data entry device 32, and, once initiated, may be executed automatically, without further user input, by the control means 20. The dark current of the photon-detector 10 may then be optionally determined to establish a base-line signal. In step 2, the reagent injector output orifice 15 is placed into operational alignment with the first well of the multi-well plate to be tested. This is accomplished by translational movement of the movable stage 13. This movement is controlled by the controller 20, and may be indexed to move accurately from well to well when multi-well plates are utilized.

Also in step 2, the reagent injector 14 is used to inject a first reagent into the well to initiate a first luminescent reaction. The luminescence of the first reaction is then measure by the photon-detector 10 in step 3. In step 4, the quantified signal is transferred via the controller 20 to the data storage and retrieval means 16 by the control lines 24 and 28.

In step 5, one or more "quench-and-activate" reagents are injected into the well by reagent injector 14. As depicted in FIGS. 3 and 4, the reagent injector includes only one reservoir. This is for clarity purposes only. The injector means may include a plurality of reservoirs from which to draw and inject various liquid and/or solid reagents into the sample wells of plate 11. The injection of the "quench-and-activate" reagent halts the first luminescent reaction, and initiates a second and distinct luminescent reaction. The luminescent energy of the second reaction is then quantified, and the signal transferred to the data storage and retrieval means 16 in steps 6 and 7 of FIG. 6.

At this point in the operation of the apparatus, two optional steps may be included: a quench reagent may be injected into the well to quench the second luminescent reaction, followed by measurement of the dark current of the photomultiplier 10. These steps may be omitted, in which case the operation of the device would proceed directly to step 10.

The entire process from steps 2 through 9 is then repeated to acquire data for the remaining sample wells. The process is repeated until all sample wells have been assayed. The data so generated is accumulated in data storage registers corresponding to the sample well tested within the data and storage retrieval means 16. In this manner, the collected data can be matched to the sample well from which it came.

The collected data is then manipulated via the control means 20, or by external data manipulation means (not shown), to yield useful information which is then displayed by the display means 30. Illustrative data manipulations would include generating ratios of the two luminescent signals per sample; means, ranges, medians, and the like between samples; curve-fitting calculations, such as least squares analyses, and non-linear curve-fitting, signal-to-noise enhancement calculations, such as Fourier transformation analysis and related manipulations; and precision, accuracy, and threshold detection calculations and compilations. Such data manipulation techniques are well-known in the art.

The present luminometer apparatus may also include components not shown which are conventionally found on luminometers. For instance, the apparatus may include a movable shutter to block the entry of light into the photomultiplier tube. This shutter can be open and closed. In the closed position, the shutter allows the dark current of the photomultiplier tube to be measured. The luminometer apparatus may include more than one type of photodetecting means in order to accurately perform assays which generate light of different wavelengths, such as U.V. light.

Figure 7:
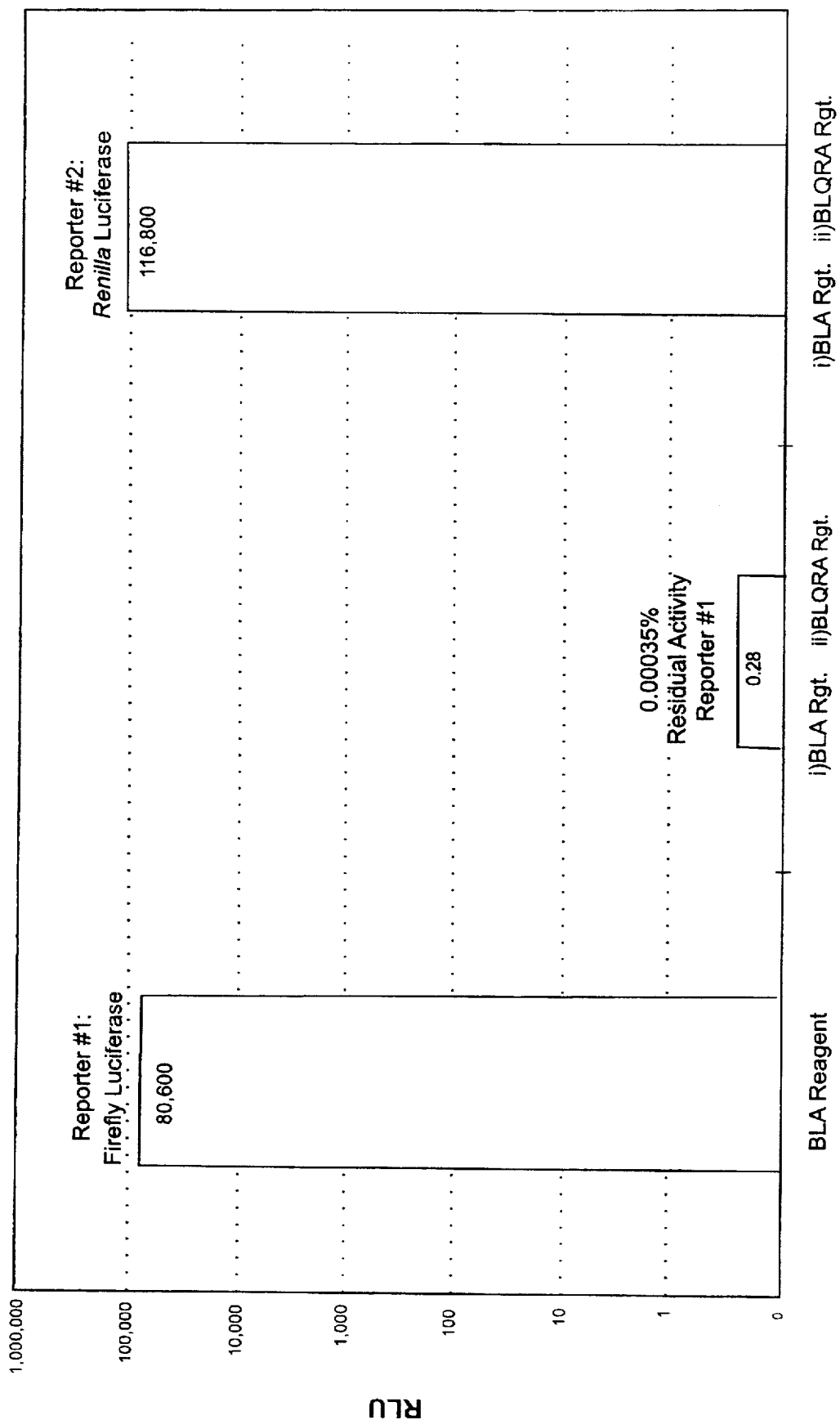
FIG. 7 shows the results of a dual-luciferase reporter assay utilizing firefly luciferase as the first reporter, and Renilla (sea pansy) luciferase as the second reporter as measured using the present invention.
Figure 8:
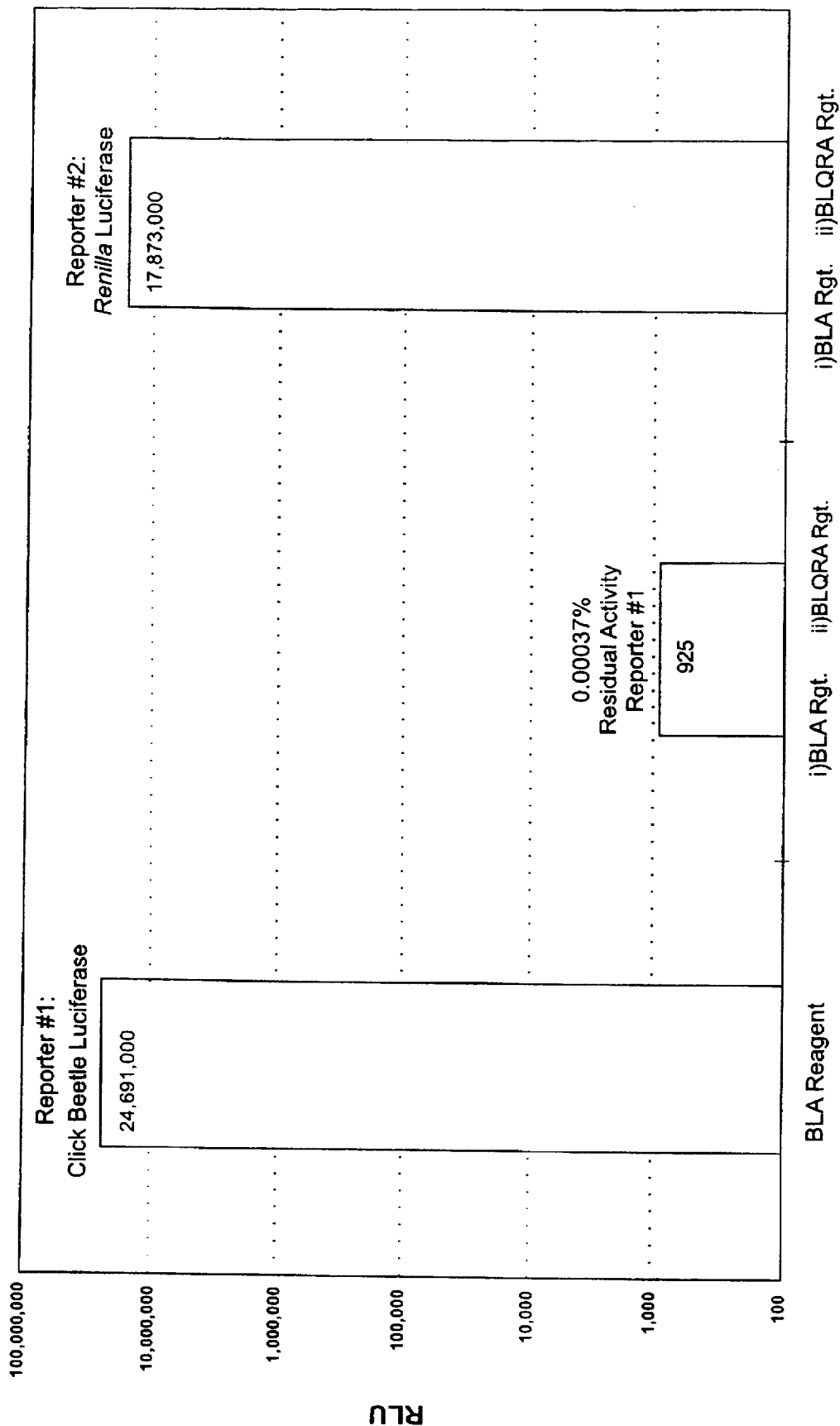
FIG. 8 shows the results of a dual-luciferase reporter assay utilizing click beetle luciferase as the first reporter, and Renilla luciferase as the second reporter as measured using the present invention.

FIGS. 7 and 8 illustrate representative dual-reporter assays utilizing firefly, Renilla, and click beetle luciferases. In FIG. 7, a first luminescent reaction, mediated by firefly luciferase was initiated and quantified. The initiating reagent is designated BLA, which is an acronym for Beetle Luciferase Activation reagent. The photons generated by this first reaction are tabulated in the left-hand column of FIG. 7. (appr. 100,000 Relative Light Units, RLU).

The first luminescent reaction was then quenched and a second, Renilla-mediated, reaction initiated by the injection of a Beetle Luciferase Quench, Renilla Luciferase Activation reagent (BLQRLA reagent). The results of this measurement are depicted in the right-hand column of FIG. 7. The center column of FIG. 7 depicts the residual activity of the first luminescent reaction when a quench reagent only is added to the sample after the initiation of the first luminescent reaction.

An analogous experiment is depicted in FIG. 8. Here, click beetle luciferase was used as the first luminescent reporter, while Renilla luciferase was used as the second luminescent reporter. The left-hand column shows initiation and quantification of the click beetle luciferase reporter. Residual activity after addition of a quench reagent only is shown in the middle column. The right-hand column shows quenching of the first luminescent reaction, and activation of a second, distinct, luminescent reaction (Renilla-mediated).

Figure 9:
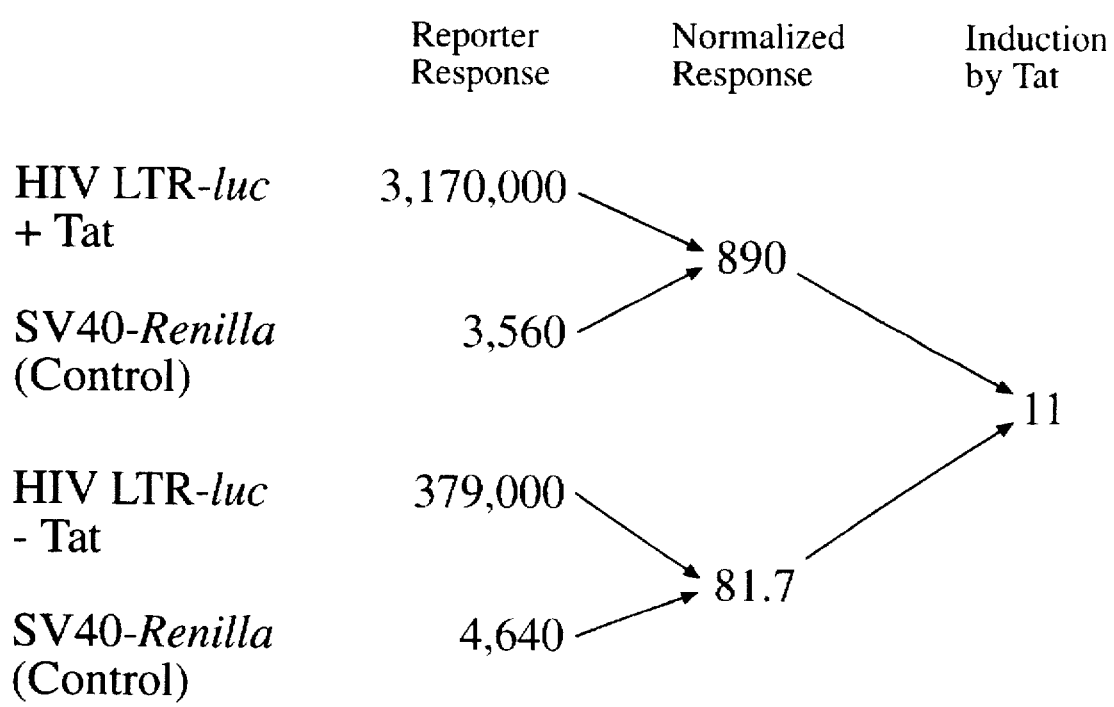
FIG. 9 shows the results of an analysis for Tat using a dual-reporter luciferase assay measured using the presently disclosed invention.

FIG. 9 depicts the results of a dual-luminescent assay for the Tat protein. An experimental genetic vector containing the firefly luciferase gene (luc) coupled to the genetic promoter of the Human Immunodeficiency Virus (HIV LTR) was introduced into a human cell line designated 293. In this experiment, the activity of the HIV LTR is expected to be activated by the Tat protein, a gene product generated during HIV replication. Also introduced as an experimental control was a genetic vector containing the Renilla luciferase gene coupled to the SV40 promoter. The SV40 promoter is expected to be unaffected by the Tat protein. The inclusion of the control vector provides an internal control for variability in the process of introducing the genetic vectors into the cells and in cell growth.

Cells containing both vectors were grown in the presence and absence of Tat in the growth medium, and subsequently lysates of the cells were made. Using the dual-luciferase reporter method, both reporters were measured from individual lysate samples. "Reporter Response" is the relative amount of luminescence measured from each lysate, and the "Normalized Response" is the ratio of the firefly luciferase assay divided by the Renilla luciferase assay. Comparison of these normalized responses indicates the amount of activation (or "Induction") caused by the Tat protein. The ratio of the normalized responses is the induction ratio.

The results also show that measurement of the first reporter does not affect the second reporter. This is true since the first reporter increases by more than 10-fold without any detectable increase in the second reporter (in fact, the second reporter is somewhat reduced, a consequence of the experimental variability described above). This is especially impressive since the first reporter yields roughly 1000-fold more luminescence than the second reporter in this particular experiment. Thus, the light from the first reporter must be quenched roughly more than 100,000-fold before measurement of the second reporter. This is as expected from the other figures (FIGS. 7 and 8) showing the quenching capacity of the quench-and-activate reagent.

The presently disclosed invention is not limited to the exact descriptions included above, but includes all equivalent embodiments thereof, accomplished by equivalent means now known, or equivalent discovered in the future.

BIBLIOGRAPHY

Blaise, C., et al. (1994) BioTechniques: 16, 932–937.
Bronstein, I., et al. (1994) Anal-Biochem.: 219, 169–181.
Denburg, et al. (1969) Archives of Biochemistry and Biophysics: 134, 381–394.
Denburg, J.L., and McElroy, W.D. (1970) Archives of Biochemistry and Biophysics: 141, 668–675.

Flanagan, W. M. et al. (1991) J. Virology: 65, 769–786.

Jain, V. K. and Magrath, I. T. (1992) BioTechniques: 12, 681–683.

Kondepudi, T., et al., Poster abstract #725, presented at annual meeting of the American Society of Cell Biology, Dec. 10–14, 1994, San Francisco, Calif.

Leckie, F. et al. (1994) BioTechniques: 17, 52–57.

Lee, et al. (1970) Archives of Biochemistry and Biophysics: 141, 38–52.

Thompson, J. F., et al. (1991) Gene: 103, 171–177.

U.S. Pat. No. 3,756,920 to Kelbaugh et al., issued Sep. 4, 1973.

U.S. Pat. No. 4,235,961 to A.T. Lundin, issued Nov. 25, 1980.

U.S. Pat. No. 4,390,274 to Berthold et al., issued Jun. 28, 1983.

U.S. Pat. No. 4,459,265 to Berglund, issued Jul. 10, 1984.

U.S. Pat. No. 4,755,055 to Johnson et al., issued Jul. 5, 1988.

U.S. Pat. No. 4,818,883 to Anderson et al., issued Apr. 4, 1989.

U.S. Pat. No. 5,035,866 to Wannlund, issued Jul. 30, 1991.

U.S. Pat. No. 5,043,141 to Wilson et al., issued Aug. 27, 1991.

U.S. Pat. No. 5,082,628 to Andreotti et al., issued Jan. 21, 1992.

U.S. Pat. No. 5,139,745 to Barr et al., issued Aug. 18, 1992.

U.S. Pat. No. 5,159,197 to Wannlund, issued Oct. 27, 1992.

U.S. Pat. No. 5,283,179, to Wood, issued Feb. 1, 1994

U.S. Pat. No. 5,290,708 to Ashihara et al., issued Mar. 1, 1994.

U.S. Pat. No. 5,316,726 to Babson et al., issued May 31, 1994.

U.S. Pat. No. 5,380,487 to Choperena et al., issued Jan. 10, 1995.

European Patent Application 0 025 350 to Holley, published Mar. 1981.

What is claimed is:

1. An apparatus for quantifying integrated photon-generating assays which utilize two distinct photon-generating reactions within a non-compartmentalized sample container, the apparatus comprising:

sample holding means dimensioned and configured to releasibly grip a non-compartmentalized sample container workpiece;

injecting means for sequentially injecting distinct first and then second reagents into the sample container workpiece at a user-defined time interval greater than zero;

a single photon measuring means for measuring photons emanating from the sample container workpiece and generating signals proportional to the measured photons, the photon measuring means dimensioned and configured to sequentially generate a first corresponding signal subsequent to injection of the first reagent into the sample container workpiece and a second corresponding signal subsequent to injection of the second reagent into the sample container workpiece;

signal storage and retrieval means for storing and retrieving the first and second signals, the signal storage and retrieval means operationally linked to the photon measuring means;

programmable control means operationally linked to and dimensioned and configured to control operation of the injecting means, the photon measuring means, and the signal storage and retrieval means, the programmable control means further dimensioned and configured to perform mathematical manipulations on the first and second signals generated by the photon measuring means; and display means to display the first and second signals and any mathematical manipulations performed thereon.

2. The apparatus according to claim 1, wherein the sample holding means is dimensioned and configured to releasibly grip a single, non-compartmentalized sample cuvette.

3. The apparatus according to claim 1, wherein the sample holding means is dimensioned and configured to releasibly grip a 96-well microtiter plate in which individual wells of the microtiter plate are non-compartmentalized.

4. The apparatus according to claim 1, wherein the injecting means comprises cooperating first and second injecting means for sequentially injecting the distinct first and then second reagents, respectively, into the sample container workpiece.

5. The apparatus according to claim 1, wherein the injecting means comprises at least two reservoirs to contain the first and second reagents, respectively, and at least two corresponding delivery means for delivering the first and second reagents from the at least two reservoirs to the sample container workpiece.

6. The apparatus according to claim 5, wherein the delivery means is selected from the group consisting of peristaltic pumps, reciprocating pumps, and vacuum aspirators.

7. The apparatus according to claim 1, wherein the photon measuring means is selected from the group consisting of single photomultiplier tubes, compound photomultiplier tubes, avalanche diodes, and charge-coupled devices.

8. The apparatus according to claim 1, wherein the programmable control means is one or more microprocessor control means.

9. The apparatus according to claim 1, wherein the injecting means includes an outflow orifice disposed adjacent to the sample container workpiece, and wherein the outflow orifice, the sample holding means, and the photon measuring means are disposed within a light-tight enclosure.

10. The apparatus according to claim 1, further comprising means for quantifying a baseline signal of the photon measuring means.

11. An apparatus for quantifying integrated photon-generating assays which utilize two distinct photon-generating reactions within a non-compartmentalized sample container, the apparatus comprising:

sample holding means dimensioned and configured to releasibly grip a non-compartmentalized sample container workpiece;

first injecting means for injecting a first reagent into the sample container workpiece;

photon measuring means for measuring photons emanating from the sample container workpiece at a user-defined time interval subsequent to injection of the first reagent and for generating a signal proportional to the measured photons;

second injecting means for injecting a second reagent into the sample container workpiece at a user-defined time interval greater than zero subsequent to injection of the first reagent;

photon measuring means for measuring photons emanating from the sample container workpiece at a user-defined time interval subsequent to injection of the second reagent and for generating a signal proportional to the measured photons, wherein the photon measuring means for measuring photons emanating from the sample container workpiece at a user-defined time interval subsequent to injection of the first reagent and the photon measuring means for measuring photons emanating from the sample container workpiece at a user-defined time interval subsequent to injection of the second reagent are one in the same;

signal storage and retrieval means for storing and retrieving the first and second signals, the signal storage and retrieval means operationally linked to the photon measuring means;

programmable control means operationally linked to and dimensioned and configured to control operation of the first and second injecting means, the photon measuring means, and the signal storage and retrieval means, the programmable control means further dimensioned and configured to perform mathematical manipulations on the first and second signals generated by the photon measuring means; and display means to display the first and second signals and any mathematical manipulations performed thereon.

12. The apparatus according to claim 11, wherein the programmable control means is one or more microprocessor control means.

13. The apparatus according to claim 11, wherein the injecting means includes one or more outflow orifices disposed adjacent to the sample container workpiece, and wherein the one or more outflow orifices, the sample holding means, and the photon measuring means are disposed within a light-tight enclosure.

* * * * *